United States Patent [19]
Poore

[11] Patent Number: 5,237,992
[45] Date of Patent: Aug. 24, 1993

[54] IMPLANTABLE PACEMAKER PROVIDING HYSTERESIS IN DUAL-CHAMBER MODES

[75] Inventor: John W. Poore, South Pasadena, Calif.

[73] Assignee: Siemens Pacesetter, Inc., Sylmar, Calif.

[21] Appl. No.: 846,308

[22] Filed: Mar. 5, 1992

[51] Int. Cl.$^5$ .............................................. A61N 1/00
[52] U.S. Cl. ......................................... 607/18; 607/25
[58] Field of Search ................................. 128/419 PG

[56] References Cited

U.S. PATENT DOCUMENTS

| | | | |
|---|---|---|---|
| 4,363,325 | 12/1982 | Roline et al. ........................ | 128/419 |
| 4,561,442 | 12/1985 | Vollmann et al. .................... | 128/419 |
| 4,562,841 | 1/1986 | Brockway et al. ................... | 128/419 |
| 4,590,944 | 5/1986 | Mann et al. ......................... | 128/419 |
| 4,712,555 | 12/1987 | Thornander et al. ................ | 128/419 |
| 4,726,380 | 2/1988 | Vollmann et al. ................... | 128/419 |
| 4,788,980 | 12/1988 | Mann et al. ......................... | 128/419 |
| 4,856,523 | 8/1989 | Sholder et al. ............... | 128/419 PG |
| 4,920,965 | 5/1990 | Funke et al. ........................ | 128/419 |
| 4,940,052 | 7/1990 | Mann et al. ......................... | 128/419 |
| 4,944,298 | 7/1990 | Sholder ............................... | 128/419 |

Primary Examiner—Lee S. Cohen
Assistant Examiner—Marianne Parker
Attorney, Agent, or Firm—Bryant R. Gold; Malcolm J. Ramano

[57] ABSTRACT

An implantable pacemaker provides three types of hysteresis for use in dual chamber and/or atrial tracking modes, such as VDI, VDD, DDI, DDD, VDIR, VDDR, DDIR or DDDR. The pacemaker defines a basic atrial escape interval (AEI) that defines the maximum time between a ventricular event and a subsequent atrial event, as well as an AV delay (AVD) that defines the maximum time between an atrial event and the next ventricular event. The sum of AEI plus AVD thus sets the rate at which stimulation pulses are generated in the absence of sensed natural cardiac activity. A first type of hysteresis, atrial escape rate hysteresis, causes the AEI to be extended upon sensing natural atrial beats (P-waves). The increased AEI remains in force so long as natural P-waves continue to be sensed during the AEI. Should a P-wave not be sensed during the AEI, a stimulation pulse is generated and the AEI reverts to its initial value. A second type of hysteresis, atrial-induced AV delay hysteresis, extends the next AVD and shortens the AEI in response to sensing a P-wave, thereby keeping the pacemaker's programmed rate the same. A third type of hysteresis, ventricular-induced AV delay hysteresis, extends the next AVD and shortens the AEI in response to sensing an R-wave. Any desired combination of the three types of hysteresis may be programmably selected for use within the pacemaker.

23 Claims, 4 Drawing Sheets $T_{Hi} = 0$    AVD HYST. NOT ENABLED
$T_{Hi} = T_{H1}$    ATRIAL INDUCED AVD EXTENSION
$= T_{H2}$    VENTRICULAR INDUCED AVD EXTENSION

A-V DELAY VALUES:

1. AVD
2. $AVD_P = AVD + T_{H1}$
3. $AVD_R = AVD + T_{H2}$

ATRIAL ESCAPE INTERNAL VALUES:

1. AEI
2. $AEI_P = AEI + T_{H3} - T_{Hi}$
   WHERE $T_{H3} > T_{Hi}$
   SO THAT
   $AEI_P > AEI$
3. $AEI_X = AEI - T_{H1}$
4. $AEI_Y = AEI - T_{H2}$

IMPLANTABLE PACEMAKER PROVIDING HYSTERESIS IN DUAL-CHAMBER MODES

BACKGROUND OF THE INVENTION

1. Field of the Invention

The present invention relates to implantable medical devices and methods, and more particularly to an implantable pacemaker that provides hysteresis in a dual chamber mode of operation that may be triggered by sensed natural rhythm occurring in either the atrium or the ventricle.

The heart is a pump that pumps life-sustaining blood through a patient's body. The heart achieves its pumping function through the contraction of its myocardial muscle tissue, which contraction squeezes the blood from one chamber of the heart to another chamber or to a specific location within the body. For example, as blood returns to the heart, after having circulated through the body, it is collected in the right atrium of the heart. Contraction of the right atrium pushes the blood held therein into the right ventricle. After a short delay, long enough to allow the blood to move from the right atrium to the right ventricle, the right ventricle contracts, forcing the blood to the patient's lungs. Blood returning from the lungs is collected in the left atrium. Contraction of the left atrium pushes the blood into the left ventricle. After a short delay, the left ventricle contracts, forcing the blood into the circulation system of the patient's body.

In a healthy heart, the right and left atria, as well as the right and left ventricles, contract simultaneously, with a short delay (e.g., 40-120 milliseconds) existing between the atrial contraction and the ventricular contraction, and a much longer delay (e.g., 350-1200 milliseconds) existing between the ventricular contraction and the next atrial contraction. It is this rhythm—of having the atria contract followed by having the ventricles contract, that is referred to as a heart "beat," or a cardiac "cycle." A typical heart may beat 85,000 to 100,000 times each day.

If the heart tissue is diseased or damaged, it may not be able to efficiently pump the blood through the body. Numerous types of maladies can occur, affecting either the ability of a given heart chamber to contract, or the timing of the myocardial muscle tissue contractions. Bradycardia, for example, is a condition of the heart where the heart beat slows to a rate that is considered insufficient to pump an adequate supply of blood through a patient's body. A heart rate of less than 50 beats per minute, for example, is usually considered as a bradycardia condition for most patients.

One common technique for treating bradycardia and other heart conditions is to implant a pacemaker in the patient. The pacemaker senses cardiac activity, i.e., heart beats, or contractions within a given heart chamber, and if the heart beats do not occur at a prescribed rate, then stimulation pulses are generated and delivered to an appropriate heart chamber, usually to either the right atrium or the right ventricle, in order to force the myocardial muscle tissue in those chambers of the heart to contract, thereby forcing the heart to beat at a faster rate or with a specified timed relationship.

In order to afford the heart every opportunity to beat on its own, i.e., to allow atrial and ventricular muscle tissue to contract naturally without external stimulation pulses, the circuits of the pacemaker define a period of time, generally referred to as the "escape interval," that is slightly longer than the period of time between heart beats of a heart beating at a minimal acceptable rate. For example, if the heart is beating at a rate of 50 beats per minute, the time period between consecutive heart beats is 1200 milliseconds. Thus, if it is desired that the heart rate never slow to a rate less than 50 beats per minute, the escape interval of the pacemaker is set to an appropriate value that causes a stimulation pulse to always be generated if more than 1200 milliseconds elapse since the last heart beat. If a heart beat occurs before 1200 milliseconds have elapsed, then the heart is beating at a rate faster than 50 beats per minute, and no stimulation pulse need be generated. Upon sensing such a "natural" (non-stimulated, sometimes referred to as "intrinsic") heart beat within the allotted time period, the escape interval is reset, and a new escape interval is started. A stimulation pulse will be generated at the conclusion of this new escape interval unless a natural heart beat is again sensed during the escape interval. In this way, stimulation pulses are generated "on demand," i.e., only when needed, in order to maintain the heart rate at a rate that never drops below the rate set by the escape interval.

The heart rate is monitored by examining the electrical signals that are manifest concurrent with the contraction of the cardiac muscle tissue in a given chamber of the heart. The contraction of atrial muscle tissue is manifest by the generation of a P-wave. The contraction of ventricular muscle tissue is manifest by the generation of an R-wave (sometimes referred to as the "QRS complex"). Because the ventricular muscle tissue is much more massive than the atrial muscle tissue, the R-wave is generally a much larger signal than the P-wave, and hence easier to detect. Advantageously, the sequence of electrical signals that represent P-waves, followed by R-waves (or QRS complexes) can be sensed by the pacemaker circuits from inside of or directly on the heart by using sensing leads implanted inside or on the heart, e.g., pacemaker leads. Such electrical signals representing internally-sensed P-waves and R-waves are referred to as the electrogram (EGM) of the heart. A dual chamber pacemaker advantageously includes means for sensing P-waves and/or R-waves, and hence means for monitoring the patient's EGM.

R-waves and/or P-waves are sensed by placing an electrode in contact with, or proximal to, the cardiac tissue of interest. Most pacemakers use the same electrode for sensing R-waves and/or P-waves as is used to deliver stimulation pulses to the corresponding ventricular and/or atrial cardiac tissue. Most modern pacemakers further include the ability, in combination with an external programming/display device in telecommunicative contact with the pacemaker, to display the EGM. A skilled cardiologist or other physician can determine a great deal about a patient's heart by simply studying the EGM of the patient. Further, the pacemaker circuits can be designed and programmed to automatically respond in an appropriate manner to various conditions manifest by the EGM.

In order to further enhance the ability of the heart to beat on its own without external stimulation, it is known in the art, when operating in certain single chamber pacing modes, to provide a longer escape interval in response to a sensed natural heart beat than is provided in response to an externally stimulated heart beat. One such single chamber pacing mode, used when sensing and pacing in the ventricle, is the VVI pacing mode. (See the next two paragraphs for a more complete description of the various pacing modes and how such modes are designated with a three or four letter code.) Thus, for example, if the pacing rate is set at 70 beats per minute (bpm), corresponding to an escape interval of 857 msec, and if no natural heart beats occur, a stimulation pulse is generated every 857 msec. Should a natural heart beat be detected, the escape interval is lengthened, e.g., by 10%, to 943 msec, in order to allow the heart to naturally beat at a rate that is slightly lower ($\approx 64$ bpm) than the 70 bpm pacing rate. In this way, the natural rhythm of the patient is given a higher priority than is the forced (paced) rhythm set by the pacemaker. The changing of the escape interval in response to sensing a natural heart beat in this manner is referred to as "hysteresis."

As indicated, heretofore hysteresis has only been used in certain single chamber pacing modes. The pacing modes of a pacemaker, both single and dual chamber pacemakers, are classified by type according to a three letter code. In such code, the first letter identifies the chamber of the heart that is paced (i.e., that chamber where a stimulation pulse is delivered), with a "V" indicating the ventricle, an "A" indicating the atrium, and a "D" indicating both the atrium and ventricle. The second letter of the code identifies the chamber wherein cardiac activity is sensed, using the same letters, and wherein an "O" indicates no sensing occurs. The third letter of the code identifies the action or response that is taken by the pacemaker. In general, three types of action or responses are recognized: (1) an Inhibiting ("I") response wherein a stimulation pulse is delivered to the designated chamber at the conclusion of the appropriate escape interval unless cardiac activity is sensed during the escape interval, in which case the stimulation pulse is inhibited; (2) a Trigger ("T") response wherein a stimulation pulse to a prescribed chamber of the heart a prescribed period of time after a sensed event; or (3) a Dual ("D") response wherein both the Inhibiting mode and Trigger mode may be evoked, e.g., with the "inhibiting" occurring in one chamber of the heart and the "triggering" in the other.

To such three letter code, a fourth letter "R" may be added to designate a rate-responsive pacemaker and/or whether the rate-responsive features of such a rate-responsive pacemaker are enabled ("O" typically being used to designate that rate-responsive operation has been disabled). A rate-responsive pacemaker is one wherein a specified parameter or combination of parameters, such as physical activity, the amount of oxygen in the blood, the temperature of the blood, etc., is sensed with an appropriate sensor and is used as a physiological indicator of what the pacing rate should be. When enabled, such rate-responsive pacemaker thus provides stimulation pulses that best meet the physiological demands of the patient.

Thus, for example, a DVI pacemaker is a pacer (note that throughout this application, the terms "pacemaker" and "pacer" are used synonymously) that paces in both chambers of the heart, but only senses in the ventricle, and that operates by inhibiting stimulation pulses when prior ventricular activity is sensed. Because it paces in two chambers, it is considered as a dual chamber pacemaker. A VVI pacer, on the other hand, is a pacer that paces only in the ventricle and senses only in the ventricle. Because only one chamber is involved, it is classified as a single chamber pacemaker. It should be noted that most dual chamber pacemakers can be programmed to operate in a single chamber mode. A DDDR pacer is a rate-responsive pacemaker that senses and paces in both chambers of the heart at a rate determined by a physiological sensor.

Heretofore, to applicant's knowledge, hysteresis has only been used in single chamber pacing modes, e.g., VVI, when cardiac activity is sensed in only one chamber of the heart. What is needed, therefore, is a hysteresis system that can be used in dual chamber pacing modes, such as DDD, or DDDR, or in other atrial tracking modes, such as VDD. The present invention advantageously provides such a system.

SUMMARY OF THE INVENTION

The present invention provides an implantable dual-chamber pacemaker and method of operating an implantable pacemaker that advantageously provides a hysteresis function in dual-chamber modes, such as DDI or DDIR, as well as in atrial tracking dual chamber modes, such as VDD, VDDR, DDD or DDDR. The hysteresis function includes three separate hysteresis modes, each of which may be selected alone or in combination with the others. The dual-chamber pacemaker, in conventional manner, defines a basic atrial escape interval (AEI) that sets the time interval between a ventricular event and an atrial event; as well as a basic AV delay (AVD) that sets the time interval or delay between an atrial event and a ventricular event. [Note, as used herein, a "ventricular event" may comprise either an R-wave or a ventricular stimulation pulse ("V-pulse"), and an "atrial event" may comprise either a P-wave or an atrial stimulation pulse ("A-pulse")]. The AEI and AVD thus combine to define a period of time that sets the "pacing rate" at which stimulation pulses are generated and delivered to a patient's heart in the absence of sensed natural cardiac activity. When the hysteresis function of the present invention is enabled, the AEI and/or the AVD are extended in response to sensed natural cardiac activity, in accordance with the particular hysteresis mode that is selected, thereby affording a longer period of time during which natural cardiac activity may occur before the pacemaker steps in to force stimulated cardiac activity.

One of the hysteresis modes provided by the invention is "atrial escape rate hysteresis". Atrial escape rate hysteresis extends the atrial escape interval, AEI, of the pacemaker by a prescribed amount in response to sensed natural atrial beats (P-waves). The increased atrial escape interval remains in force so long as natural P-waves continue to be sensed during the atrial escape interval. Should a natural P-wave not be sensed during the atrial escape interval, then an atrial stimulation pulse ("A-pulse") is generated and the AEI reverts to its programmed value, causing atrial stimulation pulses to be provided at the pacemaker's programmed pacing rate. In this manner, the patient's natural rhythm may occur at a rate that is below the programmed pacing rate. Thus, the patient's natural (intrinsic) rate is advantageously given a higher priority than is the forced (paced) rhythm provided by the pacemaker because the patient is left in natural rhythm for longer periods of time. Such action also advantageously preserves the battery life of the pacemaker because stimulation pulses are not generated as often.

Other hysteresis modes provided by the invention include atrial- or ventricular-induced AV-delay hysteresis. Such atrial- or ventricular-induced AV-delay hysteresis modes selectively extend the AVD of the pacemaker by one of two prescribed amounts. When atrial-induced AV delay hysteresis is selected, the AVD is extended a first amount in response to the occurrence of natural atrial activity, i.e., a P-wave, and the AEI is shortened a corresponding amount in order to keep the atrial pacing rate the same. The timing out of the AEI without sensing a P-wave causes an A-pulse to be generated and also causes the next AVD and AEI to revert to their original values. When ventricular-induced AV delay hysteresis only is selected, the AVD is extended a second amount in response to the occurrence of natural ventricular activity, i.e., an R-wave, and the AEI is shortened a corresponding amount in order to keep the atrial pacing rate the same. The timing out of the extended AVD without sensing an R-wave causes a V-pulse to be generated and also causes the next AVD and AEI to revert to their original values.

In accordance with one aspect of the present invention, any combination of the three hysteresis modes described above—atrial escape rate hysteresis, atrial-induced AV delay hysteresis, or ventricular-induced AV delay hysteresis—may be programmably selected for inclusion or exclusion in the operation of the dual chamber pacemaker. Hence, a significant number of hysteresis options is advantageously made possible, with each hysteresis option comprising a particular combination of inclusion or exclusion of the three possible hysteresis modes. Where the operation provided by two of the selected hysteresis modes overlaps or conflicts, appropriate rules are provided that dictate which hysteresis mode dominates the other. For example, in the event that both atrial and ventricular-induced AV delay hysteresis are selected, then the occurrence of a P-wave or an R-wave causes the AVD to be extended to the greater of the two possible AVD extension values.

Several different embodiments of the invention may advantageously be realized. Each embodiment is aimed at a dual-chamber pacemaker, or a dual-chamber pacing method, that allows stimulation pulses to be generated at a pacing rate determined by the programmed value of an atrial escape interval and AV delay, while also allowing natural atrial activity to occur at a rate less than the pacing rate.

One embodiment of the invention, for example, may be characterized as a dual-chamber programmable pacemaker that includes:

(a) timing/control means for defining an atrial escape interval (AEI) and an AV delay (AVD);

(b) programming means for setting and deriving the operating parameters of the pacemaker, including programmed values of the AEI and AVD;

(c) sensing means for sensing atrial and ventricular contractions;

(d) pulse generating means for generating an atrial stimulation pulse in response to an atrial stimulation signal; and (e) atrial escape rate hysteresis means for:

(1) extending the programmed value of the AEI by a first prescribed amount in response to sensing a natural atrial contraction by the sensing means, and (2) returning the value of the AEI to its programmed value in response to the generation of an atrial stimulation pulse by the pulse generating means, the timing/control means including means for starting the timing out of the AEI following the sensing of a ventricular contraction or the timing out of the AVD, whichever occurs first, and starting the timing out of the AEI following the sensing of an atrial contraction or the timing out of the AEI, whichever occurs first, and the timing/control means further generating the atrial stimulation signal in response to the timing out of the AEI.

Such pacemaker advantageously generates atrial stimulation pulses at a programmed rate determined by the programmed value of the AEI and AVD, yet allows natural atrial contractions to occur at a rate less than the programmed rate. Such pacemaker may also optionally include atrial-induced AV delay hysteresis means and/or ventricular-induced AV delay hysteresis means in order to selectively extend the AVD a prescribed amount.

A further embodiment of the invention may be characterized as an implantable pacemaker configured for operation in a dual-chamber pacing mode. Such implantable pacemaker includes means for sensing natural cardiac activity in the atrium and ventricle of a heart, and means for generating a stimulation pulse for delivery to a selected one of the atrium or ventricle of the heart. Such implantable pacemaker also further includes: (1) timing means for defining an atrial escape interval (AEI) and an AV delay (AVD), with the sum of the AEI and AVD comprising a first value that sets a pacer rate at which stimulation pulses are provided to the heart; and (2) programmable hysteresis means for selectively extending at least one of the AEI or AVD for so long as natural cardiac activity continues to be sensed in accordance with at least one of a plurality of hysteresis modes.

The possible hysteresis modes in accordance with this embodiment of the invention may be characterized as: (1) a first hysteresis mode (atrial escape rate hysteresis) that causes the AEI to be extended to a new value, $AEI_P$, for so long as natural cardiac activity is sensed in the atrium, with $AEI_P$ returning to AEI upon a failure to sense natural cardiac activity in the atrium; (2) a second hysteresis mode (atrial-induced AV delay hysteresis) that causes the AVD to be extended to a new value, $AVD_P$, for so long as natural cardiac activity is sensed in the atrium, with $AVD_P$ returning to AVD upon a failure to sense natural cardiac activity in the atrium; and (3) a third hysteresis mode (ventricular-induced AV delay hysteresis) that causes the AVD to be extended to a new value, $AVD_R$, for so long as natural cardiac activity is sensed in the ventricle, with $AVD_R$ returning to AVD upon a failure to sense natural cardiac activity in the ventricle.

In accordance with a variation of the second hysteresis mode, the AEI is also shortened to a new value, $AEI_X$, with the sum of $AVD_P$ and $AEI_X$ being substantially the same as the sum of AVD and AEI, for so long as natural cardiac activity is sensed in the atrium. Thereafter, $AEI_X$ is returned to AEI upon a failure to sense natural cardiac activity in the atrium.

Similarly, in accordance with a variation of the third hysteresis mode, the AEI is likewise shortened to a new value, $AEI_Y$, with the sum of $AVD_R$ and $AEI_Y$ being substantially the same as the sum of AVD and AEI, for so long as natural cardiac activity is sensed in the ventricle, with $AEI_Y$ returning to AEI upon a failure to sense natural cardiac activity in the ventricle.

Yet another embodiment of the invention may be characterized as a method of operating an implantable pacemaker operating in a dual-chamber mode of operation. Such implantable pacemaker includes means for sensing natural cardiac activity in the atrium and ventricle of a heart, as well as means for generating a stimulation pulse for delivery to a selected one of the atrium or ventricle of the heart. The method includes the steps of: (a) defining an atrial escape interval (AEI) and an AV delay (AVD), the sum of the AEI and AVD comprising a first value, the first value setting a pacer rate at which stimulation pulses are provided to the heart; and (b) selectively extending at least one of the AEI or AVD for so long as natural cardiac activity continues to be sensed in accordance with at least one of a plurality of hysteresis modes.

The plurality of hysteresis modes that may be invoked in accordance with this method include: (1) a first hysteresis mode (atrial escape rate hysteresis) that includes extending AEI to a new value, $AEI_P$, for so long as natural cardiac activity is sensed in the atrium, and returning $AEI_P$ to AEI upon a failure to sense natural cardiac activity in the atrium, (2) a second hysteresis mode (atrial-induced AV delay hysteresis) that includes extending AVD to a new value, $AVD_P$, for so long as natural cardiac activity is sensed in the atrium, and returning $AVD_P$ to AVD upon a failure to sense natural cardiac activity in the atrium, and (3) a third hysteresis mode (ventricular-induced AV delay hysteresis) that includes extending AVD to a new value, $AVD_R$, for so long as natural cardiac activity is sensed in the ventricle, and returning $AVD_R$ to AVD upon a failure to sense natural cardiac activity in the ventricle.

It is thus a primary feature of the present invention to provide a dual-chamber pacemaker, or a dual-chamber pacing method, that allows stimulation pulses to be generated at a pacing rate determined by the programmed value of an atrial escape interval and AV delay, while also allowing natural atrial and activity to occur at a rate less than the pacing rate. Such a pacemaker, or pacing method, advantageously weights the natural rhythm of the heart higher than the paced rhythm of the heart while operating in a dual chamber pacing mode, thereby affording the heart a longer time to beat on its own before stepping in with stimulation pulses that force the heart to beat at a prescribed pacing rate.

It is an additional feature of the invention to provide a dual-chamber pacemaker, or dual-chamber pacing method, that provides several different types of pacing modes that may be programmably selected for inclusion in the operation of the pacemaker.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

Figure 1:
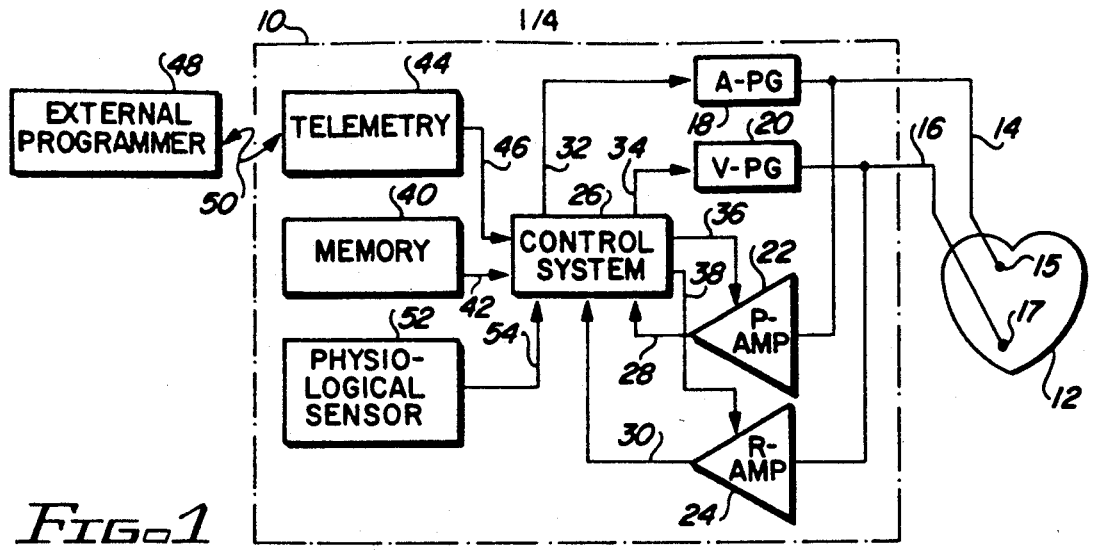
FIG. 1 is block diagram of a dual chamber programmable pacemaker.

The following description is of the best mode presently contemplated for carrying out the invention. This description is not to be taken in a limiting sense, but is made merely for the purpose of describing the general principles of the invention. The scope of the invention should be determined with reference to the claims.

Referring to FIG. a simplified block diagram of a dual chamber pacemaker 10 is illustrated. The pacemaker 10 is coupled to a heart 12 by way of leads 14 and 16, the lead 14 having an electrode 15 that is in contact with one of the atria of the heart, and the lead 16 having an electrode 17 that is in contact with one of the ventricles of the heart. The leads 14 and 16 carry stimulating pulses to the electrodes 15 and 17 from an atrial pulse generator (A-PG) 18 and a ventricular pulse generator (V-PG) 20, respectively. Further, electrical signals from the atria are carried from the electrode 15, through the lead 14, to the input terminal of an atrial channel sense amplifier (P-AMP) 22; and electrical signals from the ventricles are carried from the electrode 17, through the lead 16, to the input terminal of a ventricular sense channel amplifier (R-AMP) 24.

Controlling the dual chamber pacer 10 is a timing-/control system 26. The timing/control system 26 (referred to hereafter as simply the control system 26) receives the output signals from the atrial amplifier 22 over signal line 28. Similarly, the control system 26 receives the output signals from the ventricular amplifier 24 over signal line 30. The output signals on signal lines 28 and 30 are generated each time that a P-wave or an R-wave is sensed within the heart 12. The control system 26 also generates trigger signals that are sent to the atrial pulse generator 18 and the ventricular pulse generator 20 over signal lines 32 and 34, respectively. These trigger signals are generated each time that a stimulation pulse is to be generated by the respective pulse generator 18 or 20. The atrial trigger signal is referred to simply as the "A-pulse", and the ventricular trigger signal is referred to as the "V-pulse". During the time that either an A-pulse or V-pulse is being delivered to the heart, the corresponding amplifier, P-AMP 22 and/or R-AMP 24, is typically disabled by way of a blanking signal presented to these amplifiers from the control system over signal lines 36 and 38, respectively. This blanking action prevents the amplifiers 22 and 24 from becoming saturated from the relatively large stimulation pulses that are present at their input terminals during this time. This blanking action also helps prevent residual electrical signals present in the muscle tissue as a result of the pacer stimulation from being interpreted as P-waves or R-waves.

Still referring to FIG. 1, the pacer 10 may also include a memory circuit 40 that is coupled to the control system 26 over a suitable data/address bus 42. This memory circuit allows certain control parameters, used by the control system 26 in controlling the operation of the pacemaker, to be programmably stored and modified, as required, in order to customize the pacer's operation to suit the needs of a particular patient. Such data includes the basic timing intervals used during operation of the pacemaker, such as the programmed escape interval (EI), as well as the amount the EI is to change because of the hysteresis provided by the present invention. Further, data sensed during the operation of the pacer may be stored in the memory 40 for later retrieval and analysis.

A telemetry circuit 44 is further included in the pacer 10. This telemetry circuit 44 is connected to the control system 26 by way of a suitable command/data bus 46. In turn, the telemetry circuit 44, which is included within the implantable pacer 10, may be selectively coupled to an external programming device 48 by means of an appropriate communication link 50, which communication link 50 may be any suitable electromagnetic link, such as an RF (radio frequency) channel. Advantageously, through the external programmer 48 and the communication link 50, desired commands may be sent to the control system 26. Similarly, through this communication link 50 and the programmer 48, data (either held within the control system 26, as in a data latch, or stored within the memory 40, may be remotely received from the pacer 10. In this manner, non-invasive communications can be established with the implanted pacer 10 from a remote, non-implanted, location.

The pacer 10 in FIG. 1 is referred to as a dual chamber pacemaker because it interfaces with both the atria and the ventricles of the heart. Those portions of the pacer 10 that interface with the atria, e.g., the lead 14, the P-wave sense amplifier 22, the A-pulse generator 18, and corresponding portions of the control system 26, are commonly referred to as the atrial channel. Similarly, those portions of the pacer 10 that interface with the ventricles, e.g., the lead 16, the R-wave sense amplifier 24, the V-pulse generator 20, and corresponding portions of the control system 26, are commonly referred to as the ventricular channel.

In accordance with one embodiment of the present invention, the pacemaker 10 further includes a physiological sensor 52 that is connected to the control system 26 of the pacer over a suitable connection line 54. While this sensor 52 is illustrated in FIG. 1 as being included within the pacer 10, it is to be understood that the sensor may also be external to the pacer 10, yet still be implanted within or carried by the patient. A common type of sensor is an activity sensor, such as a piezoelectric crystal, mounted to the case of the pacemaker. Other types of physiologic sensors are also known, such as sensors that sense the oxygen content of blood, respiration rate, pH of blood, body motion, and the like. The type of sensor used is not critical to the present invention. Any sensor capable of sensing some physiological parameter relatable to the rate at which the heart should be beating can be used. Such sensors are commonly used with "rate-responsive" pacemakers in order to adjust the rate (escape interval) of the pacer in a manner that tracks the physiological needs of the patient.

Figures 2, 3:
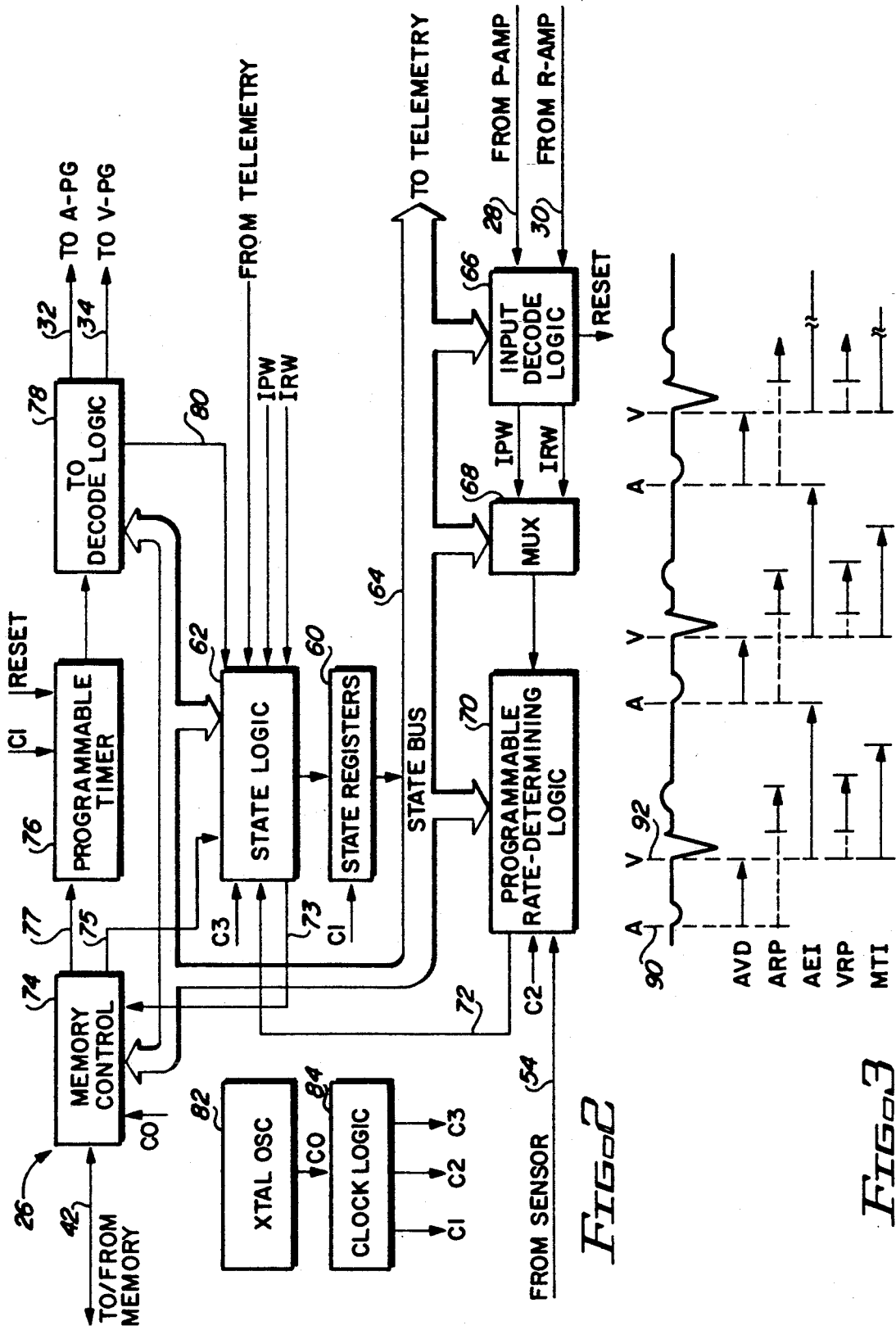
FIG. 2 is a block diagram of one possible embodiment of the control logic of the pacemaker of FIG. 1.
FIG. 3 is a timing diagram that defines the basic time intervals associated with the operation of a dual-chamber pacemaker.

Referring next to FIG. 2, a block diagram of one embodiment of the control system 26 of the pacer 10 is illustrated. It is noted that other embodiments of a control system 26 may also be utilized, such as a microprocessor-based control system. A representative microprocessor-based system is described, for example, in U.S. Pat. No. 4,940,052, entitled "Microprocessor Controlled Rate-Responsive Pacemaker Having Automatic Threshold Adjustment." The '052 patent is assigned to the same assignee as is this application, and is incorporated herein by reference.

The control system shown in FIG. 2 is based on a state machine wherein a set of state registers 60 define the particular state of the pacer at any instant in time. In general, and as an overview of state machine operation, each state, by design, causes a certain activity or function to be carried out. Several states are executed in a sequence during a given cardiac cycle. The sequence of states that is executed in a particular cardiac cycle is determined by the particular events that occur, such as the sensing of a P-wave or an R-wave, as well as the current state, as certain states can only be entered from certain other states. Only one state can exist at any instant of time, although several different state machines (or control systems) may operate in parallel to control diverse functions. For example, the telemetry circuit 44 (FIG. 1) preferably utilizes its own state machine, such as is described in the above-cited patent. This telemetry circuit state machine operates essentially independent of the control system state machine of FIG. 2.

At the heart of the control system 26 is the state logic 62. It is the state logic that controls the "state" of the state registers 60, and hence the function or operation that will next be carried out by the system. The state logic 62 receives as inputs the current state of the state registers, made available over a state bus 64 (which state bus directs the state of the system to several sections of the control system), as well as other signals indicating the current status of the system or events that have occurred. The output signals from the P-AMP 22 (FIG. 1) and the R-AMP 24 (FIG. are directed to an input decode logic circuit 66. This circuit generates appropriate logic signals "IPW" (Inhibiting P-Wave) and "IRW" (Inhibiting R-Wave) that are selected by a multiplexer 68 and sent to rate-determining logic 70. These signals are also sent to the state logic 62. The function of the rate-determining logic 70 is to determine the rate at which either the IPW or IRW signals are occurring. A signal representative of this rate is sent, as an output signal from the rate determining logic 70, to the state logic 62 over signal line 72. Rate-determining logic 70 further receives a sensor rate signal from the sensor 52 (FIG. 1), and (depending upon the particular state of the system, as defined by the state registers 60, and as made available to the rate-determining logic 70 over the state bus 64) sends a rate signal to the state logic 62 over signal line 72 indicative of this sensor rate.

Still referring to FIG. 2, a memory control circuit 74 provides the needed interface between the circuits of the control system 26 and the memory 40 (FIG. 1). This memory control circuit may be any conventional memory access circuit that sends or receives data to or from memory at a specified address. Data retrieved from memory 40 may be sent to either the state logic 62 (over signal line(s) 75) or to a programmable timer 76 (over signal line(s) 77). Data sent to memory 40 may be either the current state of the system (obtained off of the state bus 64), or other selected signals from the state logic (as made available over signal line(s) 78).

The programmable timer 76 defines a prescribed time interval, the length of which is set by the signal(s) received from the memory control 74 over signal line(s) 77, and the starting point of which begins coincident with the start of the current state, as obtained from the state bus 64. The timer 76 further generates a time out (T.O.) signal when this prescribed time interval has elapsed. During this prescribed time interval, the timing function may be reset by a reset signal, typically obtained from the input decode logic 66, although some states (as obtained from the state bus 64) may also effectuate an immediate reset of the timer 76. The time out signal is sent to time out decode logic 78. It is the function of the time out decode logic to generate the appropriate trigger signals that are sent to the A-pulse generator 18 or the V-pulse generator 20 (FIG. 1). Further, an appropriate logic signal(s) is sent to the state logic 62 by the time out decode logic 78 over signal line(s) 80 in order to notify the state logic that the respective trigger signals have been generated.

An oscillator 82, preferably a crystal-controlled oscillator, generates a basic clock signal C0 that controls the operation of the system logic. This clock signal C0 is sent to clock logic circuits 84, where other appropriate clock signals, such as clock signals C1, C2, and C3, are generated, all derived from the basic clock signal C0. These clock signals are distributed throughout the control system 26 in order to appropriately synchronize the various events and state changes that occur within the pacemaker. The rate of the basic clock signal C0 is not critical to the present invention. In general, a rate of 25-40 Khz for the basic clock rate C0 is adequate. This rate provides a basic time increment of 25-40 microseconds each clock cycle, and this is more than enough time to effectively control the pacemaker operation. If desired, a faster basic clock rate can be used, particularly by the memory control 74, to speed up the data transfer between the control system 26 and the memory 40, although for most pacemaker operations, a fast data transfer rate is not essential.

In operation, the control system of FIG. 2 starts at an initial state, wherein the state registers 60 assume a prescribed value that defines the initial state. For example, assuming four flip flops are used for the state registers 60, an initial state might be "1000" (hexadecimal "8") wherein the first flip flop assumes a "1" state, and the remaining three flip flops each assume a "0" state. This state may be defined as a V-A Delay (VAD) state wherein a prescribed ventricular-to-atrial (V-A) interval is initiated. This V-A interval may be considered as the "atrial escape interval", or "AEI". As soon as the memory control 74 detects that the VAD state has been initiated, as evidenced by the "1000" appearing on the state bus 64, it retrieves from the memory 40 an appropriate data word, previously programmed into the memory 40 from the external programmer 48, that defines the desired length of the AEI. This data word is sent to the programmable timer and sets the length of the time period that is to be measured during the VAD state.

The timer 76 is essentially just a counter that counts down (or counts up), using a specified clock signal, to the value specified in the data word. When the counting has been completed, and assuming that the counter has not been reset by the occurrence of a P-wave, the counter or timer 76 is said to have "timed out", and an appropriate time out signal is generated that is sent to the time out decode logic 78. The decode logic, in turn, recognizes that the current state of the system is the VAD state (as determined by monitoring the state bus 64), and therefore that the AEI has timed out without any cardiac activity having been sensed. Hence, an A-pulse trigger signal is generated and sent to the A-pulse generator 18, so that the atrium can be stimulated. At the same time, an appropriate logic signal(s) is sent to the state logic 62 over the signal line(s) 80 to alert the state logic to the fact that the timer 76 has timed out.

The state logic 62, in response to receiving the signal(s) from the time out decode logic 78, and also in response to the current VAD state, triggers the next state of the prescribed sequence. For DDD operation, this state is typically a blanking state, or BLANK state, during which the P and R sense amplifiers, 22 and 24, are disabled. Accordingly, the state logic generates appropriate signal(s) on signal lines 36 and 38 to blank the P-wave sense amplifier 22 and the R-wave sense amplifier 24, and also causes the state registers 60 to change to a BLANK state, which state could be defined, for example, by the flip flops of the state registers 62 assuming a "0001" (hex "1") condition. This BLANK state, detected on the state bus 64, causes the memory control circuitry to retrieve an appropriate data word from memory that defines the length of the blanking interval, which data word is loaded into the programmable timer 76. As soon as the timer 76 times out, indicating that the prescribed blanking interval has elapsed, a time out signal is generated that is sent to the time out decode logic 78. Upon receipt of this time out signal, and in response to the current state being a BLANK state, the time out decode logic 78 sends an appropriate logic signal to the state logic 62. The state logic 62 responds by steering the state registers 62 to assume the next state in the prescribed sequence, which may be, for example, an AV Delay state.

At the beginning of the AV Delay state, another value is loaded into the programmable timer 76 that defines the length of the AV delay, or "AVD". If the timer 76 times out without being reset, indicating that no R-wave has been sensed, the decode logic generates a V-pulse trigger signal, and notifies the state logic 62 of this event. The state logic, in turn, causes the next appropriate state to be entered, which state may be another blanking state, or BLANK state, similar to the one described above, but having perhaps a different duration. At the conclusion or timing out of this second BLANK state, the next state in the prescribed sequence is initiated, which state may be a refractory (REF) state.

In the manner described above, the control system 26 assumes one state after another, thereby controlling the operation of the pacemaker. In general, a state is changed when the timer 76 times out, or when a prescribed event occurs. Further, in accordance with the present invention, if a prescribed event occurs, e.g., the occurrence of a P-wave, and if an appropriate hysteresis mode is enabled, the programmed value of the pacer's basic atrial escape interval, AEI, and/or the pacer's AVD, is changed, as explained more fully below.

It is noted that the state of the control system could also be changed by receipt of an appropriate command from the telemetry system.

The control system 26 of FIG. 2 may be realized using dedicated hardware circuits, or by using a combination of hardware and software (or firmware) circuits. The appropriate sequence of states for a given mode of operation, such as DDD or VDI, for example, can be defined by appropriate control of the memory control 74 and the state logic 62. These circuit elements, in turn, are most easily controlled through an appropriate software or firmware program that is placed or programmed into the pacemaker memory circuits. The manner of accomplishing such programming is known in the art.

A detailed description of the various circuits of the control system 26 of FIG. 2 will not be presented herein because all such circuits may be conventional, or may be patterned after known circuits available in the art. Reference is made, for example, to U.S. Pat. No. 4,712,555 wherein a state-machine type of operation for a pacemaker is described; U.S. Pat. No. 4,788,980, wherein the various timing intervals used within the pacemaker and their inter-relationship are more thoroughly described; and U.S. Pat. No. 4,944,298 wherein an atrial-rate based programmable pacemaker is described, including a thorough description of the operation of the state logic used to control such a pacemaker. The '298 patent is incorporated herein by reference.

Referring next to FIG. 3, a timing diagram depicting the basic timing signals associated with the operation of a dual-chamber pacemaker is illustrated. An understanding of the interrelationship between these basic timing signals, particularly between the atrial escape interval (AEI) and the AV delay, AVD, will be most helpful in the description of the hysteresis modes of the invention presented below. It should also be noted that not all of the timing signals or time periods associated with the operation of a dual-chamber pacemaker are included in FIG. 3, e.g., blanking intervals are not included. Rather, only the main timing signals are shown.

As seen in FIG. 3, the occurrence of an A-pulse 90, generated to cause the atrium to contract, starts an AV-delay, AVD, and an atrial refractory period, ARP. Both the AVD and the ARP have programmed values that are determined, e.g., in the manner described above using a counter circuit, or equivalent. During the timing out of the AVD, the sensing circuits of the pacemaker monitor the ventricular sense amplifier to determine if an R-wave (natural ventricular activity) has occurred. During the timing out of the ARP, the atrial sensing circuits are refractory, meaning they are not capable of sensing atrial activity during this time. (Actually, as those skilled in the pacing arts will realize, the ARP is divided into two portions: an absolute refractory portion during which no atrial activity can be sensed, indicated in FIG. 3 as a dashed line; and a relative refractory portion during which atrial activity may be sensed, but is treated as noise, indicated as a solid line.)

If the AVD "times out" without sensing an R-wave, then a V-pulse 92 is generated to stimulate the ventricle and force a ventricular contraction. For most pacemakers, the timing out of the AVD triggers at least four events: (1) the generation of the V-pulse 92 to stimulate the ventricle; (2) the starting of the atrial escape interval, AEI; (3) the starting of the ventricular refractory period, VRP (which is also divided into absolute and relative portions as is the ARP); and (4) the starting of the maximum tracking interval, MTI. The VRP defines that period of time during which an R-wave (natural ventricular activity) may not be sensed. The MTI defines the shortest period of time that may exist between a V-pulse and an A-pulse or P-wave, and thus defines, when combined with the AVD, the maximum rate at which the pacer may stimulate the heart. The AEI defines the longest period of time that may exist between ventricular activity (a V-pulse or R-wave) and the next atrial activity (an A-pulse or P-wave). and thus defines, when combined with the AVD, the programmed pacer rate at which the pacer stimulates the heart.

For the condition shown in FIG. 3, the cardiac cycle that includes the A-pulse 90 and the V-pulse 92 repeats itself, with the AVD and ARP intervals starting at the timing out of the preceding AEI; and with the AEI, VRP and MTI starting at the timing out of the preceding AVD. In this manner, stimulation pulses are provided to the heart at a rate determined by the AVD and AEI. It is noted that no natural cardiac activity (P-waves or R-waves) is shown in FIG. 3.

In accordance with the present invention, a hysteresis function is advantageously included in an implantable pacemaker configured to operate in a dual-chamber mode. Such hysteresis function adjusts the AVD and/or the AEI in order to extend the appropriate interval so as to afford additional time for natural cardiac activity to be sensed before a stimulation pulse is generated. This is done in the manner depicted in FIG. 4.

Figure 4:
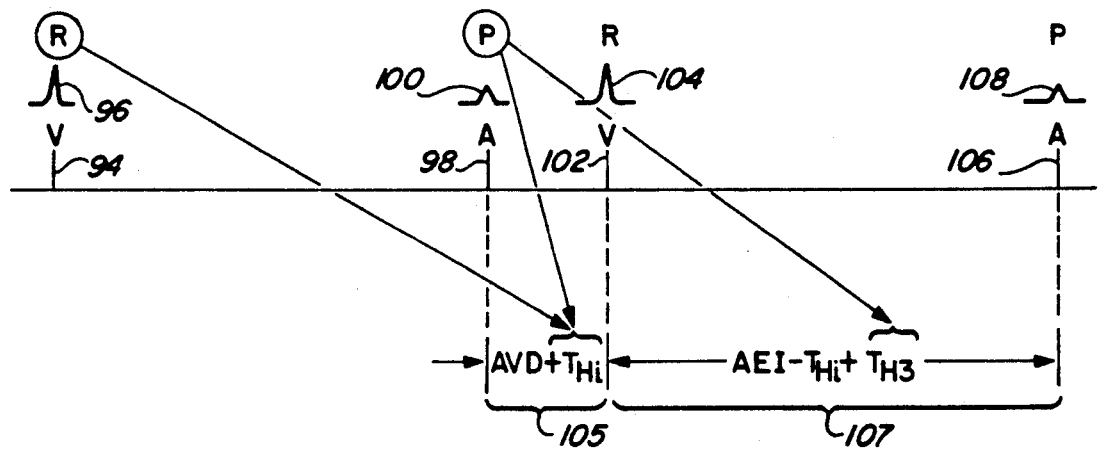
FIG. 4 is an expanded timing diagram that illustrates how the present invention selectively alters the AEI and/or the AVD in accordance with the various hysteresis modes of the invention.

In FIG. 4, the basic timing sequence associated with consecutive cardiac cycles is illustrated as a time line across the top of the figure. A V-pulse 94 or R-wave 96 represents ventricular activity of a prior cardiac cycle. An A-pulse 98 or P-wave 100 represents atrial activity of a beginning cardiac cycle. A first time interval 105 separates the next ventricular activity, which could be a V-pulse 102 or an R-wave 104, from the A-pulse 98 or the P-wave 100. A second time interval 107 separates the succeeding atrial activity, A-pulse 106 or P-wave 108, from the V-pulse 102 or R-wave 104. Note that during normal paced operation, i.e., when A-pulses and V-pulses are generated, the first time interval 105 is the AVD, and the second time interval 107 is the AEI. During non-paced operation, i.e., when naturally occurring P-waves and R-waves are present, the first time interval 105 is less than AVD, and the second time interval 107 is less than AEI.

In accordance with a first hysteresis mode of the present invention, referred to as atrial escape rate hysteresis, the occurrence of a P-wave 100 extends the AEI by a prescribed amount $T_{H3}$ to a new value $AEI_P$. Such extension affords a longer time for a natural P-wave 108 to occur, and has the effect of slowing down the atrial rate.

In accordance with a second hysteresis mode of the present invention, referred to as atrial-induced AV delay hysteresis, the occurrence of a P-wave 100 extends the AVD by a prescribed amount $T_{H1}$ to a new value $AVD_P$, thus affording a longer time for an R-wave 104 to occur. In a preferred variation of the atrial-induced AV delay hysteresis mode, the extending of AVD to $AVD_P$ is also accompanied by the shortening of AEI by an amount $T_{H1}$ to a new value $AEI_X$. Thus, the sum of $AVD_P$ and $AEI_X$ is the same as the sum of AVD and AEI, and thus the atrial rate of the pacemaker does not change.

In accordance with a third hysteresis mode of the present invention, referred to as ventricular-induced AV delay hysteresis, the occurrence of an R-wave 96 extends the next AVD 105 by a prescribed amount $T_{H2}$ to a new value $AVD_R$, thus affording a longer time for an R-wave 104 to occur. In a preferred variation of the ventricular-induced AV delay hysteresis mode, the extending of AVD to $AVD_R$ is also accompanied by the shortening of AEI by an amount $T_{H2}$ to a new value $AEI_Y$. Thus, the sum of $AVD_R$ and $AEI_Y$ is the same as the sum of AVD and AEI, and thus the atrial rate of the pacemaker does not change.

Thus, as illustrated in FIG. 4, during atrial-or ventricular-induced AV delay hysteresis, the AVD interval 105 may be extended by an amount $T_{Hi}$, where $T_{Hi}$ is $T_{H1}$ when atrial-induced AV delay hysteresis is enabled (thus making $AVD_P = AVD + T_{H1}$), and where $T_{Hi}$ is $T_{H2}$ when ventricular-inducted AV-delay hysteresis is enabled (thus making $AVD_R = AVD + T_{H2}$). The value of AEI may then be shortened by the corresponding $T_{Hi}$ ($T_{H1}$ or $T_{H2}$) in order to keep the overall pacing rate the same.

During atrial escape rate hysteresis, the AEI interval is extended by an amount $T_{H3}$ to $AEI_P$. As seen in FIG. 4, $AEI_P = AEI + T_{H3} - T_{Hi}$. The value of $T_{Hi}$ enters into the determination in the event that atrial- or ventricular-induced hysteresis is enabled jointly with atrial escape rate hysteresis. That is, it is an important feature of the invention that any of the three hysteresis modes may be programmably selected alone or in combination with the other hysteresis modes. Thus, if both atrial escape rate hysteresis and atrial-induced AV delay hysteresis are enabled at the same time, for example, then the AEI is shortened by an amount $T_{H1}$ (in accordance with the atrial-induced AV delay hysteresis) and lengthened by an amount $T_{H3}$ (in accordance with the atrial escape rate hysteresis). In such case, it is preferred that $T_{H3}$ be greater than $T_{H1}$ so that the overall effect of the two hysteresis modes is to lengthen the AEI.

If both atrial-induced and ventricular-induced AV delay hysteresis are enabled at the same time, then the value of $T_{Hi}$ used to extend the AVD 105 is $T_{H1}$ in response to the most recent P-wave 100, or $T_{H2}$ (if $T_{H2}$ is greater than $T_{H1}$) in response to the most recent R-wave 96. A corresponding value of $T_{Hi}$ is used to shorten AEI 107 in such situation.

Table 1 summaries the various combinations of hysteresis modes that are possible with the present invention. As seen in Table 1, eight possible combinations are possible, including the situation where all three hysteresis modes are not enabled. The eight possible combinations are denominated in Table 1 with a number ranging from 0 to 7. The number shown may be used as a shorthand way of indicating the particular hysteresis modes that are enabled—atrial escape rate hysteresis, atrial-induced AV delay hysteresis, or ventricular-induced AV delay hysteresis. Thus, for example, a reference to hysteresis "mode 2" signifies that atrial-induced AV delay hysteresis is enabled, and atrial escape rate hysteresis and ventricular-induced AV delay hysteresis are not enabled. Similarly, hysteresis "mode 7" signifies that all three hysteresis modes are enabled.

Advantageously, the amount of hysteresis to be utilized in any given mode, e.g., the value of $T_{Hi}$, may be specified as a time (msec), a percent (%) of the relevant time interval, or (for the atrial escape interval, AEI) as a prescribed number of pulses per minute (PPM).

TABLE 1

| Dual Chamber Hysteresis Modes | | | | |
|---|---|---|---|---|
| Atrial Escape Rate Hyst. | Atrial-Induced AV Delay Hyst. | Ventrclr-Induced AV Delay Hyst. | Hyst. Mode | Description of Action Taken |
| OFF | OFF | OFF | 0 | Normal Pacer Operation |
| OFF | OFF | ON | 1 | AVD lengthened to $AVD_R$ in response to R-wave, and AEI shortened to keep atrial rate the same. |
| OFF | ON | OFF | 2 | AVD lengthened to $AVD_P$ in response to P-wave, and AEI shortened to keep atrial rate the same. |
| OFF | ON | ON | 3 | AVD lengthened to $AVD_P$ in response to the most recent P-wave, or to $AVD_R$ (if $AVD_R > AVD_P$) in response to the most recent R-wave, and AEI shortened to keep atrial rate the same. |
| ON | OFF | OFF | 4 | AEI lengthened to $AEI_P$ in response to P-wave; no change in AVD; atrial rate thereby made slower. |
| ON | OFF | ON | 5 | AVD lengthened to $AVD_R$ in response to R-wave, and AEI lengthened to $AEI_P$ in response to P-wave. |
| ON | ON | OFF | 6 | AVD lengthened to $AVD_P$ and AEI lengthened to $AEI_P$ in response to P-wave. |
| ON | ON | ON | 7 | AVD lengthened to $AVD_P$ in response to the most recent P-wave, or to $AVD_R$ (if $AVD_R > AVD_P$) in response to the most recent R-wave, and AEI lengthened to $AEI_P$ in response to P-wave. |

Figure 5:
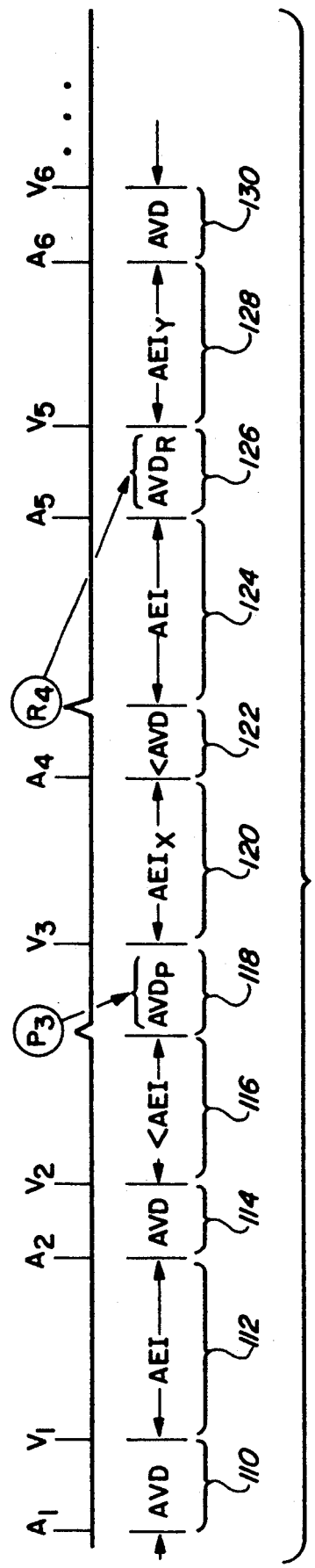
FIG. 5 is a timing sequence diagram that depicts the atrial-induced AV delay hysteresis mode in combination with the ventricular-induced AV delay hysteresis mode of the invention.

Turning next to FIG. 5, there is shown a timing sequence diagram that depicts an example of the operation of the atrial-induced AV delay hysteresis mode in combination with the ventricular-induced AV delay hysteresis mode. This combination corresponds to "mode 3" as described in Table 1. As seen in FIG. 5, a first A-pulse $A_1$ causes the time period AVD 110 to start. The timing out of AVD 110 without sensing natural ventricular activity causes V-pulse $V_1$ to be generated and starts the atrial escape interval AEI 112. The timing out of AEI 112 without sensing natural atrial activity causes a second A-pulse $A_2$ to be generated and starts the next AVD 114. AVD 114, in sequence, times out without natural ventricular activity being sensed, thereby causing V-pulse $V_2$ to be generated, and starting the next atrial escape interval 116. Before the interval 116 times out, i.e., at a time that is less than AEI, a P-wave $P_3$ is sensed.

The occurrence of the natural P-wave $P_3$ triggers the atrial-induced AV delay hysteresis mode of the present invention, causing the next AV delay 118 to begin, and increasing its value by an amount $T_{H1}$ to $AVD_P$. $AVD_P$ times out, causing a V-pulse $V_3$ to be generated and starts the next atrial escape interval 120. The occurrence of P$_3$ causes the value of the next atrial escape interval 120 to be decreased by an amount T$_{H1}$ to AVD$_X$. Note that the basic atrial pacing rate, determined by the sum of AEI and AVD does not change in this instance because the amount by which the AVD is increased is the same amount by which the AEI is decreased.

In accordance with the atrial-induced AV delay hysteresis mode, the extended AVD$_P$ and shortened AEI$_X$ continue for so long as natural atrial cardiac activity (P-waves) continues to be sensed. However, for the situation shown in FIG. 5, no natural atrial activity is sensed before AEI$_X$ 120 times out. Therefore, an A-pulse A$_4$ is generated and the next AV delay 122 is started. Before the AV delay 122 times out, i.e., at a time less than AVD, an R-wave R$_4$ is sensed. This R-wave R$_4$, in accordance with the ventricular-induced AV delay hysteresis mode of the invention, causes the next AV delay, 126, to be increased by an amount T$_{H2}$ to AVD$_R$, followed by an atrial escape interval 128 that is decreased by the amount T$_{H2}$ to AEI$_Y$. Again, the basic atrial pacing rate does not change because the amount by which the AVD is increased is the same amount by which the AEI is decreased.

In accordance with the ventricular-induced AV delay hysteresis mode, the extended AVD$_R$ and shortened AEI$_Y$ continue for so long as natural ventricular cardiac activity (R-waves) continues to be sensed. However, for the situation shown in FIG. 5, no natural ventricular activity is sensed before AVD$_R$ 126 times out, therefore the ventricular-induced AV delay hysteresis terminates after the last AEI$_Y$ triggered by such ventricular-induced AV delay hysteresis times out. Thus, V-pulse V$_5$ is generated, followed by A-pulse A$_6$ after the timing out of AEI$_Y$ 128, followed by V-pulse V$_6$ after the timing out of the next AVD 130.

Figure 6:
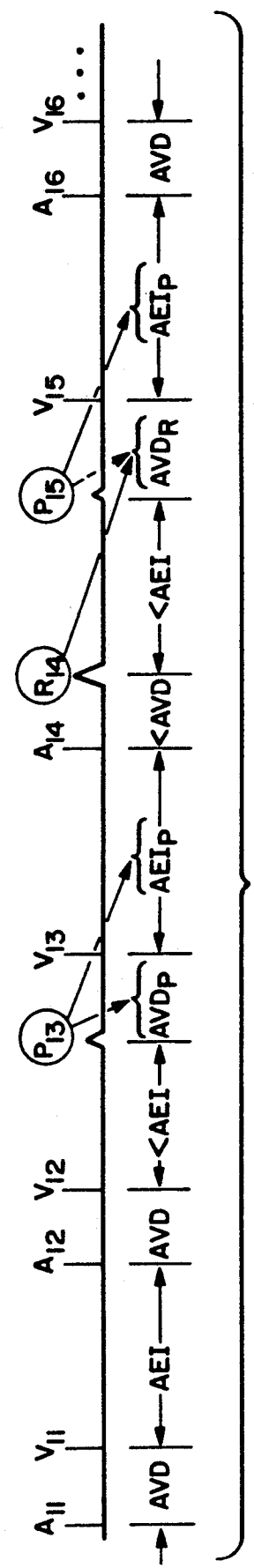
FIG. 6 is a timing sequence diagram as in FIG. 5, but further includes the atrial escape rate hysteresis mode.

Turning next to FIG. 6, a timing sequence diagram as in FIG. 5 is shown, but further including the atrial escape rate hysteresis mode as well as the atrial- and ventricular-induced AV delay hysteresis modes. FIG. 6 thus corresponds to "mode 7" in Table 1. As seen in FIG. 6, the sequence follows a normal paced pattern up to the occurrence of P-wave P$_{13}$. The occurrence of P$_{13}$ triggers both the atrial-induced AV delay hysteresis, causing the next AV delay to be increased to AVD$_P$, and the atrial escape rate hysteresis, causing the following atrial escape interval to be increased to AEI$_P$.

The extended values of AVD$_P$ and AEI$_P$ continue for so long as natural atrial activity is detected. For the situation shown in FIG. 6, the AEI$_P$ interval times out without detecting another P-wave, causing A-pulse A$_{14}$ to be generated, and further causing the effects of both the atrial-induced AV delay hysteresis and the atrial escape rate hysteresis terminate. However, before the next AVD following A$_{14}$ times out, R-wave R$_{14}$ is sensed, triggering the ventricular-induced AV delay hysteresis, which causes the next AV delay to be increased to AVD$_R$. Further, before the atrial escape interval following R$_{14}$ times out, P-wave P$_{15}$ is sensed, causing the next AV delay, already extended to AVD$_R$ by the occurrence of R$_{14}$, to be extended to the greater of AVD$_R$ or AVD$_P$. The P-wave P$_{15}$ also causes the next atrial escape interval to be extended to AEI$_P$. Note that R-wave R$_{14}$ followed by P-wave P$_{15}$ causes the longest possible pacing interval, i.e., the extended AEI$_P$ followed by the extended AVD$_R$.

By way of example, assume that "mode 7" is enabled for a pacer operating in the DDDR pacing mode. The programmed pacing rate is 70 ppm, the atrial escape rate hysteresis is programmed at 10%, the AV delay, AVD, is set at 150 msec, the atrial-induced AV delay hysteresis is set at 10%, and the ventricular-induced AV delay hysteresis is set at 20%. Hence, with reference to FIG. 6, the value of AVD is 150 msec, and the value of AEI is 707 msec (70 ppm=857 msec; so AVI=857−150 =707 msec). The value of AVD$_P$ is 165 msec (T$_{H1}$=10% of 150 msec, or 15 msec, making AVD$_P$=150+15=165 msec). The value of AVD$_R$ is 180 msec (T$_{H2}$=20% of 150 msec, or 30 msec, making AVD$_R$=150+30 =180 msec). The value of AEI$_P$ is 787 msec (10% of 70 ppm=7 ppm, making the atrial escape hysteresis rate=63 ppm; 63 ppm corresponds to a period of 952 msec; T$_{H1}$ is 15 msec, and the AVD$_P$ portion of this 952 msec is 165 msec, leaving 787 msec as AEI$_P$). The value of T$_{H3}$ is 95 msec (AEI$_P$=787=T$_{H3}$+AEI −T$_{H1}$, and T$_{H3}$=787−707+15=95 msec) It is to be emphasized that the above numbers are only exemplary. It is also to be emphasized that the value of AEI, as well as the value of AVD, will change as a function of the sensor-indicated rate for a rate responsive pacing mode. Hence, the above numbers would also be changed accordingly.

Figure 7:
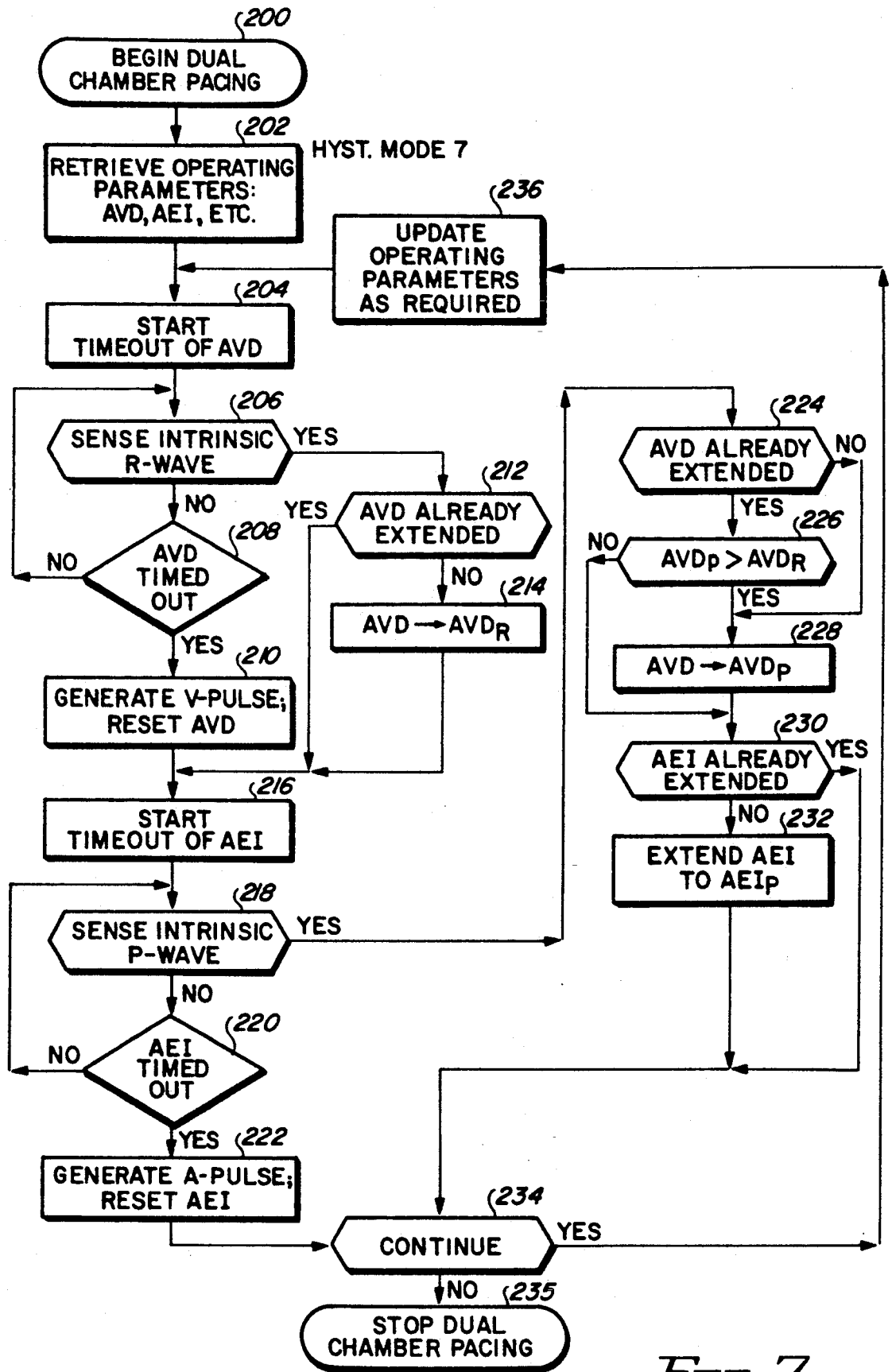
FIG. 7 is a flow chart depicting the hysteresis method of the present invention for the situation where all three hysteresis modes are selected.

Referring next to FIG. 7, there is shown a simplified flow chart depicting the hysteresis method of the present invention for the situation where all three hysteresis modes are selected, i.e., for "mode 7" in Table 1. Similar flow charts may be readily derived for the other modes in Table 1, given the information presented in Table 1 and elsewhere herein. Each main step of the method is depicted in FIG. 7 as a "block," with each block having a reference number associated thereof to assist in the explanation that follows.

As seen in FIG. 7, once the desired dual chamber pacing mode has been selected, as indicated at block 200, a first step of the method involves retrieving the appropriate operating parameters for the hysteresis mode that has been selected (block 202). As indicated, FIG. 7 assumes that the hysteresis mode is mode 7 (see Table 1). Such parameters define such variables as AVD, AEI, T$_{H1}$, T$_{H2}$, and T$_{H3}$. Such parameters may be either retrieved directly from memory, or calculated from other parameters that have been previously stored in memory, or otherwise made available for retrieval.

Once the operating parameters have been retrieved, the timeout of the AVD is stated (block 204). While the AVD is timing out, a determination is made as to whether a natural (intrinsic) R-wave has been sensed (block 206). If no R-wave is detected when AVD times out (block 208), then a V-pulse is generated and AVD and AEI is reset (block 210). To reset AVD means to return AVD to its initial value from an extended value, if it has been previously extended. If the AEI has previously been shortened, e.g. to AEI$_Y$, then such AEI would also be reset at this time.

If an R-wave is detected (block 206) during the time out of the AVD, then a determination is made as to whether the AVD has already been extended (block 212). If not, the AVD is extended to AVD$_R$. At this same time, the AEI may be shortened to AEI$_Y$ if such shortening is desired.

After the generation of a V-pulse and the resetting of AVD (block 210), or the extending of AVD to AVD$_R$ (block 214), the timeout of the AEI is started (block 216). During the time out of the AEI, a determination is made as whether natural atrial activity has been sensed (block 218). If not, and if the AEI has timed out (block 220), then an A-pulse is generated. and the AEI is reset (block 222). To "reset AEI" means to return AEI to its initial value from an extended value.

Following the generation of the A-pulse (block 222), a decision may be made as to whether the process is to continue (block 234). If not, the method terminates (block 235). If so, the operating parameters are updated (block 236), as required, and the process repeats beginning at block 204. Updating of parameters may be periodically required, for example, if the pacing mode is a rate responsive mode, and the values of AVD and AEI may be changing based on a sensor indicated rate.

If a natural P-wave is sensed during the timing out of the AEI (block 218), then an initial determination is made as to whether the AVD has already been extended (block 224). For example, the AVD may have already been extended to $AVD_R$ at block 214. If the AVD has been extended, then a determination is made as to whether AVD, is greater than $AVD_R$ (block 226). If so, then AVD is extended to $AVD_P$ (block 228). If not, then AVD remains at $AVD_R$. If the AVD has not been extended, as determined at block 224, then it is extended to $AVD_P$ (block 228). In this manner, the AVD is extended an appropriate amount—to the larger of $AVD_R$ or $AVD_P$ if previously extended to $AVD_R$, or to $AVD_P$—in response to the sensing of a P-wave during the time out of AEI.

Once the AVD has been extended an appropriate amount, a determination is made as to whether the AEI has already been extended (block 230). If not, then AEI is extended to $AEI_P$ (block 232). If already extended, then no further extension is necessary.

With AEI extended to $AEI_P$, the process is ready to repeat. That is, a determination is made as to whether the process should continue (block 234). If so, the operating parameters are updated as required (block 236) and the process repeats beginning at block 204. If not, then the method terminates (block 235).

As described above, it is thus seen that the present invention provides a dual-chamber pacemaker, or a dual-chamber pacing method, that allows stimulation pulses to be generated at a pacing rate determined by the programmed value of an atrial escape interval and AV delay, while also allowing natural atrial activity to occur at a rate less than the pacing rate. Such a pacemaker, or pacing method, thus advantageously weights the natural rhythm of the heart higher than the paced rhythm of the heart, thereby affording the heart a longer time to beat on its own before stepping in with stimulation pulses that force the heart to beat at a prescribed pacing rate.

As further described above, it is seen that the present invention further provides a dual-chamber pacemaker, or dual-chamber pacing method, that advantageously provides several different pacing modes that may be programmably selected for inclusion or exclusion in the operation of the pacemaker.

While the invention herein disclosed has been described by means of specific embodiments and applications thereof, numerous modifications and variations could be made thereto by those skilled in the art without departing from the scope of the invention set forth in the claims.

What is claimed is:

1. A dual-chamber programmable pacemaker comprising:

(a) timing/control means for defining an atrial escape interval (AEI) and an atrial ventricular delay (AVD);
    (b) programming means for setting and deriving operating parameters of said pacemaker, including programmed values of said AEI and AVD;
    (c) sensing means for sensing atrial and ventricular contractions;
    (d) pulse generating means for generating an atrial stimulation pulse;
    (e) atrial escape rate hysteresis means for:
        (1) extending the programmed value of the AEI by a first prescribed amount in response to sensing a natural atrial contraction by said sensing means, and
        (2) returning the value of the AEI to its programmed value in response to the generation of an atrial stimulation pulse by said pulse generating means, said timing/control means including means for starting the timing out of said AEI following the sensing of a ventricular contraction or the timing out of said AVD, whichever occurs first, and starting the timing out of said AEI following the sensing of an atrial contraction or the timing out of said AEI, whichever occurs first, said pulse generating means further generating said atrial stimulation pulse in response to the timing out of the AEI, whereby atrial stimulation pulses are generated by said dual-chamber pacemaker at a programmed rate determined by the programmed value of the AEI and AVD, and natural atrial contractions are allowed to occur at a rate less than the programmed rate; and (f) atrial-induced AVD hysteresis means for:
        (1) extending the programmed value of the AVD by a second prescribed amount in response to sensing a natural atrial contraction by said sensing means, said second prescribed amount being less than said first prescribed amount, and shortening the programmed value of the AEI by said second prescribed amount, and
        (2) returning the value of the extended AVD to its programmed value in response to the generation of an atrial stimulation pulse by said pulse generating means.

2. The pacemaker, as set forth in claim 1, wherein said pulse generating means further comprises means for generating a ventricular stimulation pulse, said ventricular stimulation pulse generated at the timing out of the AVD, said pacemaker further including ventricular-induced AVD hysteresis means for:

(1) extending the programmed value of the AVD by a third prescribed amount in response to sensing a natural ventricular contraction by said sensing means, said third prescribed amount being less than said first prescribed amount, and shortening the programmed value of the AEI by said third prescribed amount, and
    (2) returning the value of the extended AVD to its programmed value in response to the generation of a ventricular stimulation pulse by said pulse generating means.

3. The pacemaker, as set forth in claim 2, wherein said programming means comprises means for selectively enabling and disabling said atrial escape rate hysteresis means, said atrial-induced AVD hysteresis means, and said ventricular-induced AVD hysteresis means, whereby selected combinations of said atrial escape rate hysteresis means, said atrial-induced AVD hysteresis means, and said ventricular-induced AVD hysteresis means may be enabled for use within said pacemaker.

4. The pacemaker, as set forth in claim 3, further comprising means for combining said atrial-induced AVD hysteresis means and said ventricular-induced AVD hysteresis means when both are enabled through said programming means such that said AVD is extended by the greater of said second prescribed amount or said third prescribed amount, and said AEI is shortened by the greater of said second prescribed amount or said third prescribed amount.

5. The pacemaker, as set forth in claim 3, further comprising means for combining said atrial-induced AVD hysteresis means and said ventricular-induced AVD hysteresis means when both are enabled through said programming means such that said AVD is first extended by the second or third prescribed amount as a function of whether natural atrial or natural ventricular activity is sensed first, respectively, and is thereafter extended by the greater of said second or third prescribed amount only upon the occurrence of the respective natural atrial or natural ventricular activity corresponding to the greater of said second or third prescribed amounts, and said AEI is shortened by the same second or third prescribed amount used to extend said AVD.

6. The pacemaker, as set forth in claim 3, wherein said pacemaker further comprises physiological sensing means for sensing a physiological parameter, said physiological parameter providing an indication of the physiological need of a patient, and wherein said timing/control means further comprises means for automatically adjusting said programmed AEI in response to the physiological parameter sensed by said physiological sensing means.

7. The pacemaker, as set forth in claim 6, wherein said timing/control means comprises a programmable timer that defines a time interval having a duration set by a control variable applied thereto, and wherein said control means applies a first control variable to said programmable timer to define said AEI, and a second control variable to said programmable timer to define an extended AEI.

8. The pacemaker, as set forth in claim 7, wherein said programmable timer comprises a digital counter and a clock circuit, and wherein said control variable comprises a digital data word that is loaded into said digital counter, the time interval defined by said programmable timer comprising the time it takes said digital data word to be counted by said digital counter and clock circuit.

9. An implantable pacemaker configured for operation in a dual-chamber pacing mode, said pacemaker comprising:
   means for sensing natural cardiac activity in the atrium and ventricle of a heart, and means for generating a stimulation pulse for delivery to a selected one of the atrium or ventricle of the heart;
   timing means for defining an atrial escape interval (AEI) and an atrial ventricular delay (AVD), the sum of said AEI and AVD comprising a first value, said first value setting a pacer rate at which stimulation pulses are provided to the heart; and
   programmable hysteresis means for selectively extending at least one of said AEI or AVD for so long as natural cardiac activity continues to be sensed in accordance with at least one of a plurality of hysteresis modes.

10. The implantable pacemaker, as set forth in claim 9, wherein said plurality of hysteresis modes comprises:
   a first hysteresis mode that causes the AEI to be extended to a new value, $AEI_P$, for so long as natural cardiac activity is sensed in the atrium, with $AEI_P$ returning to AEI upon a failure to sense natural cardiac activity in the atrium; and
   a second hysteresis mode that causes the AVD to be extended to a new value, $AVD_P$, for so long as natural cardiac activity is sensed in the atrium, with $AVD_P$ returning to AVD upon a failure to sense natural cardiac activity in the atrium.

11. The implantable pacemaker, as set forth in claim 10, wherein said second hysteresis mode further causes AEI to be shortened to a new value, $AEI_X$, with the sum of $AVD_P$ and $AEI_X$ being substantially the same as the sum of AVD and AEI, for so long as natural cardiac activity is sensed in the atrium, with $AEI_X$ returning to AEI upon a failure to sense natural cardiac activity in the atrium.

12. The implantable pacemaker, as set forth in claim 10, wherein said plurality of hysteresis modes further comprises a third hysteresis mode that causes the AVD to be extended to a new value, $AVD_R$, for so long as natural cardiac activity is sensed in the ventricle, with $AVD_R$ returning to AVD upon a failure to sense natural cardiac activity in the ventricle.

13. The implantable pacemaker, as set forth in claim 12, wherein said third hysteresis mode further causes AEI to be shortened to a new value, $AEI_Y$, with the sum of $AVD_R$ and $AEI_Y$ being substantially the same as the sum of AVD and AEI, for so long as natural cardiac activity is sensed in the ventricle, with $AEI_Y$ returning to AEI upon a failure to sense natural cardiac activity in the ventricle.

14. The implantable pacemaker, as set forth in claim 9, wherein said plurality of hysteresis modes comprises:
   a first hysteresis mode that causes the AEI to be extended to a new value, $AEI_P$, for so long as natural cardiac activity is sensed in the atrium, with $AEI_P$ returning to AEI upon a failure to sense natural cardiac activity in the atrium; and
   a third hysteresis mode that causes the AVD to be extended to a new value, $AVD_R$, for so long as natural cardiac activity is sensed in the ventricle, with $AVD_R$ returning to AVD upon a failure to sense natural cardiac activity in the ventricle.

15. The implantable pacemaker, as set forth in claim 14, wherein said third hysteresis mode further causes AEI to be shortened to a new value, $AEI_Y$, with the sum of $AVD_P$ and $AEI_Y$ being substantially the same as the sum of AVD and AEI, for so long as natural cardiac activity is sensed in the ventricle, with $AEI_Y$ returning to AEI upon a failure to sense natural cardiac activity in the ventricle.

16. The implantable pacemaker, as set forth in claim 9, wherein said plurality of hysteresis modes comprises:
   a second hysteresis mode that causes the AVD to be extended to a new value, $AVD_P$, for so long as natural cardiac activity is sensed in the atrium, with $AVD_P$ returning to AVD upon a failure to sense natural cardiac activity in the atrium; and
   a third hysteresis mode that causes the AVD to be extended to a new value, $AVD_R$, for so long as natural cardiac activity is sensed in the ventricle, with $AVD_R$ returning to AVD upon a failure to sense natural cardiac activity in the ventricle.

17. The implantable pacemaker, as set forth in claim 16 wherein said second hysteresis mode further causes AEI to be shortened to a new value, $AEI_X$, with the sum of $AVD_P$ and $AEI_X$ being substantially the same as the sum of AVD and AEI, for so long as natural cardiac activity is sensed in the atrium, with $AEI_X$ returning to AEI upon a failure to sense natural cardiac activity in the atrium.

18. The implantable pacemaker, as set forth in claim 16, wherein said third hysteresis mode further causes AEI to be shortened to a new value, $AEI_Y$, with the sum of $AVD_P$ and $AEI_Y$ being substantially the same as the sum of AVD and AEI, for so long as natural cardiac activity is sensed in the ventricle, with $AEI_Y$ returning to AEI upon a failure to sense natural cardiac activity in the ventricle.

19. The implantable pacemaker, as set forth in claim 9, further comprising physiological sensing means for sensing a physiological parameter indicative of how fast the heart should beat, and wherein said timing means comprises means for selectively defining said first value of said escape interval as a function of the physiological parameter sensed by said physiological sensing means.

20. A method of operating an implantable pacemaker configured for operation in a dual-chamber pacing mode, said pacemaker comprising means for sensing natural cardiac activity in the atrium and ventricle of a heart, and means for generating a stimulation pulse for delivery to a selected one of the atrium or ventricle of the heart, said method comprising the steps of:
   (a) defining an atrial escape interval (AEI) and an AV delay (AVD), the sum of said AEI and AVD comprising a first value, said first value setting a pacer rate at which stimulation pulses are provided to the heart; and
   (b) selectively extending at least one of said AEI or AVD for so long as natural cardiac activity continues to be sensed in accordance with at least one of a plurality of hysteresis modes, said plurality of hysteresis modes comprising:
      (1) a first hysteresis mode that comprises extending AEI to a new value, $AEI_P$, for so long as natural cardiac activity is sensed in the atrium, and returning $AEI_P$ to AEI upon a failure to sense natural cardiac activity in the atrium,
      (2) a second hysteresis mode that comprises extending AVD to a new value, $AVD_P$, for so long as natural cardiac activity is sensed in the atrium, and returning $AVD_P$ to AVD upon a failure to sense natural cardiac activity in the atrium, and
      (3) a third hysteresis mode that comprises extending AVD to a new value, $AVD_R$, for so long as natural cardiac activity is sensed in the ventricle, and returning $AVD_R$ to AVD upon a failure to sense natural cardiac activity in the ventricle.

21. The method of operating a pacemaker, as set forth in claim 20, wherein said second hysteresis mode further comprises shortening AEI to a new value, $AEI_X$, so that the sum of $AVD_P$ and $AEI_X$ is substantially the same as the sum of AVD and AEI, for so long as natural cardiac activity is sensed in the atrium, and returning $AEI_X$ to AEI upon a failure to sense natural cardiac activity in the atrium.

22. The method of operating a pacemaker, as set forth in claim 20, wherein said third hysteresis mode further comprises shortening AEI to a new value, $AEI_Y$, so that the sum of $AVD_R$ and $AEI_Y$ is substantially the same as the sum of AVD and AEI, for so long as natural cardiac activity is sensed in the atrium, and returning $AEI_Y$ to AEI upon a failure to sense natural cardiac activity in the atrium.

23. A dual-chamber programmable pacemaker comprising:
   (a) timing/control means for defining an atrial escape interval (AEI) and an atrial ventricular delay (AVD);
   (b) programming means for setting and deriving operating parameters of said pacemaker, including programmed values of said AEI and AVD;
   (c) sensing means for sensing atrial and ventricular contractions;
   (d) pulse generating means for generating an atrial stimulation pulse;
   (e) atrial escape rate hysteresis means for:
      (1) extending the programmed value of the AEI by a first prescribed amount in response to sensing a natural atrial contraction by said sensing means, and
      (2) returning the value of the AEI to its programmed value in response to the generation of an atrial stimulation pulse by said pulse generating means,
said timing/control means including means for starting the timing out of said AEI following the sensing of a ventricular contraction or the timing out of said AVD, whichever occurs first, and starting the timing out of said AEI following the sensing of an atrial contraction or the timing out of said AEI, whichever occurs first, said pulse generating means further generating said atrial stimulation pulse in response to the timing out of the AEI, whereby atrial stimulation pulses are generated by said dual-chamber pacemaker at a programmed rate determined by the programmed value of the AEI and AVD, and natural atrial contractions are allowed to occur at a rate less than the programmed rate.

* * * * *